United States Patent
Ranucci et al.

(10) Patent No.: US 9,675,353 B2
(45) Date of Patent: Jun. 13, 2017

(54) SURGICAL FASTENERS AND ASSOCIATED DEPLOYMENT DEVICES

(71) Applicant: C.R. Bard, Inc., Murray Hill, NJ (US)

(72) Inventors: Kevin J. Ranucci, Warwick, RI (US); Saurav V. Gupta, Medway, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 14/075,398

(22) Filed: Nov. 8, 2013

(65) Prior Publication Data

US 2015/0133964 A1    May 14, 2015

(51) Int. Cl.
*A61B 17/08* (2006.01)
*A61B 17/10* (2006.01)
(Continued)

(52) U.S. Cl.
CPC ............. *A61B 17/10* (2013.01); *A61B 17/068* (2013.01); *A61B 17/08* (2013.01); *A61B 2017/0649* (2013.01)

(58) Field of Classification Search
CPC ....... A61B 17/08; A61B 17/10; A61B 17/068; A61B 17/105; A61B 2017/00305; A61B 2017/00314; A61B 2017/0649; A61B 17/0443; A61B 17/064; A61B 17/888; A61B 17/8883; A61B 17/8886; A61B 17/8888; A61B 17/8891; B25B 19/00; B25B 23/04; B25B 23/08; B25B 23/10; F16B 37/12
(Continued)

(56) References Cited

U.S. PATENT DOCUMENTS 2,407,879 A   9/1946   Haas
3,229,374 A   1/1966   Comorau
(Continued)

FOREIGN PATENT DOCUMENTS

EP   0 663 184   7/1995
GB   2417208     2/2006
(Continued)

OTHER PUBLICATIONS

Winding. (n.d.). Dictionary.com Unabridged. Retrieved Apr. 14, 2016 from Dictionary.com website http://www.dictionary.com/browse/winding.*

*Primary Examiner* — Jonathan Miles
*Assistant Examiner* — Kankindi Rwego
(74) *Attorney, Agent, or Firm* — Wolf, Greenfield & Sacks, P.C.

(57) ABSTRACT

A surgical fastener and a related deployment device as well as their methods of use are disclosed. In one embodiment, the deployment device includes one or more surgical fasteners including a head and a distally extending coil body attached to the head. The head includes a through hole with an internal thread. The deployment device also includes a mandrel including a threaded portion located at a distal end of the mandrel. The threaded portion is engaged with the internal thread of the one or more surgical fasteners. A rotator is associated with the one or more surgical fasteners such that the rotator can selectively rotate the one or more surgical fasteners relative to the mandrel to displace the one or more surgical fasteners in a distal direction.

15 Claims, 4 Drawing Sheets

(51) Int. Cl.
*A61B 17/068* (2006.01)
*A61B 17/064* (2006.01)

(58) Field of Classification Search
USPC .......................................................... 606/151
See application file for complete search history.

(56) References Cited

U.S. PATENT DOCUMENTS

| | | | |
|---|---|---|---|
| 4,318,651 A * | 3/1982 | Ragen | F16B 37/12 411/342 |
| 4,762,453 A | 8/1988 | DeCaro | |
| 4,917,554 A | 4/1990 | Bronn | |
| 5,904,696 A | 5/1999 | Rosenman | |
| 6,383,187 B2 | 5/2002 | Tormala et al. | |
| 6,409,445 B1 | 6/2002 | Beale et al. | |
| 7,189,251 B2 | 3/2007 | Kay | |
| 7,862,573 B2 * | 1/2011 | Darois | A61B 17/064 606/139 |
| 7,867,252 B2 | 1/2011 | Criscuolo et al. | |
| 8,087,142 B2 | 1/2012 | Levin et al. | |
| 8,231,639 B2 | 7/2012 | Bolduc et al. | |
| 8,292,933 B2 | 10/2012 | Zergiebel | |
| 8,343,176 B2 | 1/2013 | Criscuolo et al. | |
| 8,382,778 B2 | 2/2013 | Criscuolo et al. | |
| 9,072,511 B2 | 7/2015 | Tegzes | |
| 2003/0181913 A1 | 9/2003 | Lieberman et al. | |
| 2004/0193217 A1 | 9/2004 | Lubbers et al. | |
| 2005/0187568 A1 * | 8/2005 | Klenk | A61B 17/0057 606/153 |
| 2007/0038220 A1 | 2/2007 | Shipp | |
| 2007/0088390 A1 | 4/2007 | Paz et al. | |
| 2007/0140810 A1 | 6/2007 | Itou et al. | |
| 2007/0250064 A1 | 10/2007 | Darois et al. | |
| 2010/0010520 A1 * | 1/2010 | Takahashi | A61B 17/064 606/157 |
| 2010/0256690 A1 | 10/2010 | Appenzeller et al. | |
| 2010/0274266 A1 | 10/2010 | Rimer et al. | |
| 2011/0087240 A1 | 4/2011 | Shipp | |
| 2011/0092992 A1 | 4/2011 | Darois et al. | |
| 2011/0295282 A1 * | 12/2011 | Glick | A61B 17/064 606/151 |
| 2011/0295319 A1 | 12/2011 | Duplessis et al. | |
| 2012/0022557 A1 | 1/2012 | Cabiri et al. | |
| 2012/0101526 A1 | 4/2012 | Bennett | |
| 2013/0131700 A1 | 5/2013 | Criscuolo et al. | |
| 2014/0243855 A1 | 8/2014 | Sholev et al. | |
| 2015/0133970 A1 | 5/2015 | Ranucci et al. | |
| 2015/0133971 A1 | 5/2015 | Ranucci et al. | |
| 2015/0133972 A1 | 5/2015 | Ranucci et al. | |
| 2015/0152908 A1 | 6/2015 | Schwarzbich | |

FOREIGN PATENT DOCUMENTS

| | | |
|---|---|---|
| WO | WO 97/07744 | 3/1997 |
| WO | WO 02/09625 | 2/2002 |
| WO | WO 2005/004727 | 1/2005 |
| WO | WO 2005/081936 | 9/2005 |
| WO | WO 2011/092692 | 8/2011 |
| WO | WO 2012/176195 | 12/2012 |
| WO | WO 2013/046115 | 4/2013 |
| WO | WO2013046115 * | 4/2013 |

* cited by examiner

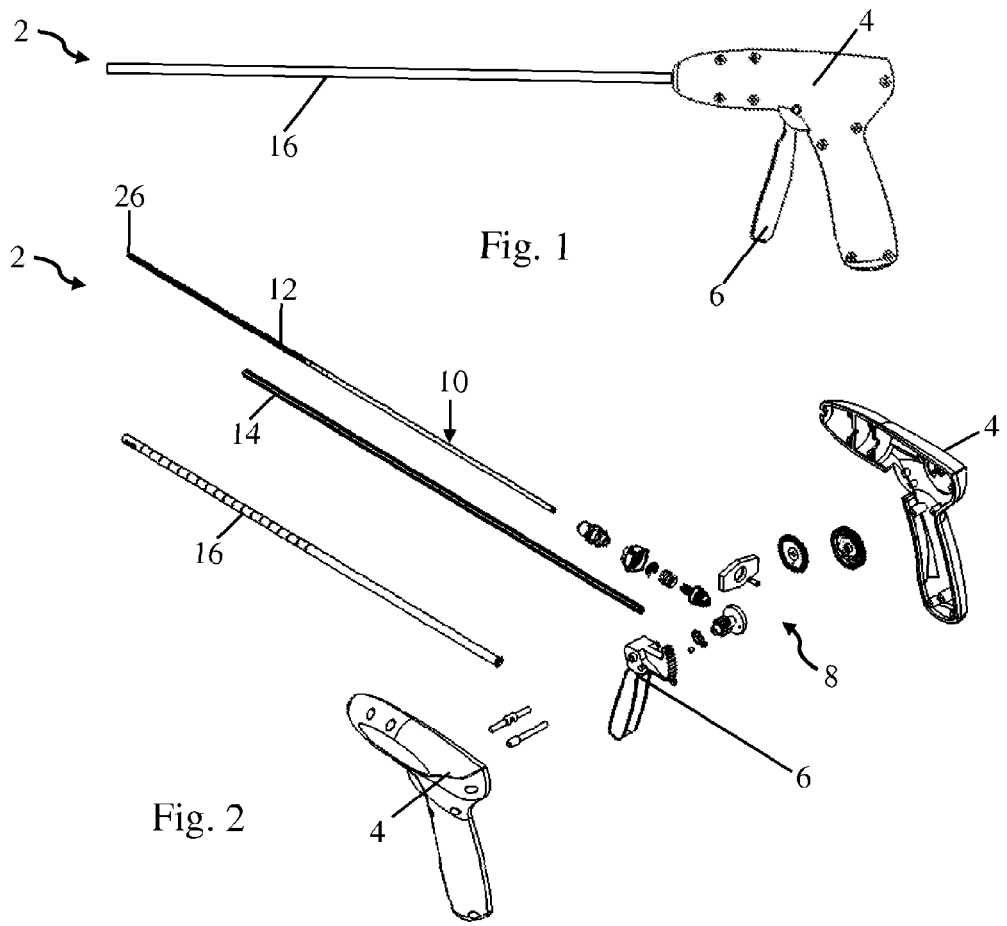
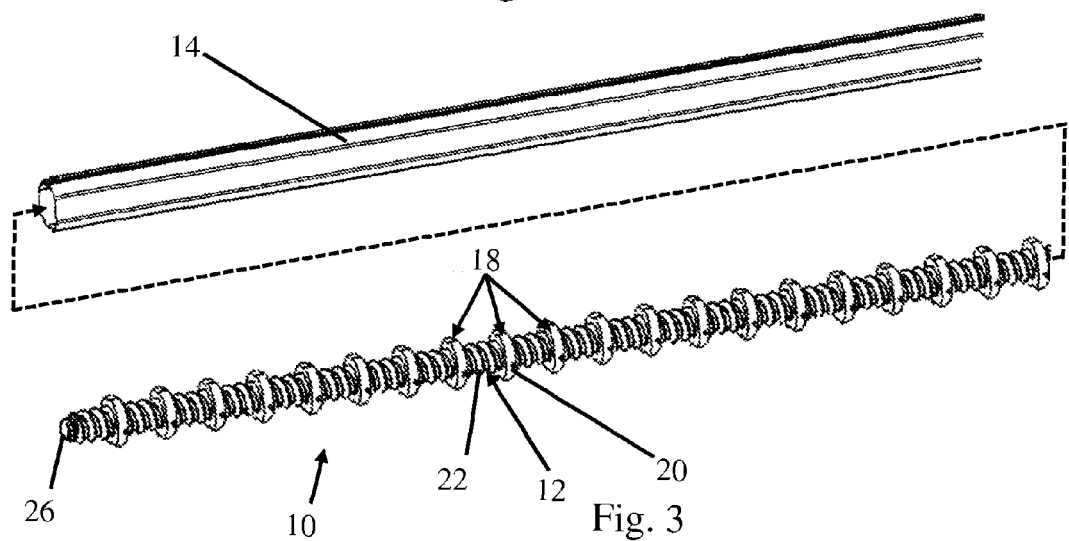

SURGICAL FASTENERS AND ASSOCIATED DEPLOYMENT DEVICES

FIELD

Disclosed embodiments are related to surgical fasteners and associated deployment devices.

BACKGROUND

Surgical fasteners are widely used in many different medical procedures. For example, staples, sutures, clips and other fasteners are commonly used in laparoscopic and open surgical procedures.

SUMMARY

In one embodiment, a deployment device includes a handle and a shaft extending distally from the handle. One or more surgical fasteners including a head and a distally extending coil body attached to the head may be disposed in the shaft. The head includes a through hole with an internal thread. The deployment device also includes a mandrel including a threaded portion. The threaded portion is engaged with the internal thread of the head of the one or more surgical fasteners. A rotator is associated with the one or more surgical fasteners, wherein the rotator selectively rotates the one or more surgical fasteners relative to the mandrel to displace the one or more surgical fasteners in a distal direction.

In another embodiment, a surgical fastener includes a head including a through hole with an internal thread and a distally extending coil body attached to the head.

In yet another embodiment, a method includes: rotating one or more surgical fasteners relative to a mandrel in a surgical fastener deployment system, wherein the one or more fasteners include a head and a distally extending coil body attached to the head, wherein the head includes a through hole with an internal thread, and wherein the mandrel includes a threaded portion constructed and arranged to engage with the internal thread of the head of the one or more surgical fasteners, and wherein rotating the one or more surgical fasteners relative to the mandrel displaces the one or more surgical fasteners in a distal direction down the surgical fastener deployment instrument.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 1 is a schematic representation of a deployment device;

FIG. 2 is a schematic perspective exploded view of the deployment device depicted in FIG. 2;

FIG. 3 is a schematic perspective exploded view of the outer drive cannula and the mandrel holding a plurality of fasteners;

DETAILED DESCRIPTION

Coil fasteners typically do not include a fastener head which may result in the uncovered top coil winding contacting adjacent tissue. Further, in instances where a conventional coil fastener is overdriven, the coil fastener may go through an intended prosthetic material and/or tissue it is meant to engage since there is no structure present to prevent the top coil from passing through the prosthetic material and/or tissue. Consequently, the inventors have recognized the benefits of a fastener including a distally extending coil body including one or more coil windings that is attached to an associated fastener head. Such a fastener offers the benefit of reduced insertion resistance associated with a coil fastener while including a head to avoid the coil body from contacting adjacent tissue and prevent the coil body from passing through the intended prosthetic material and/or tissue. Additionally, the fastener head provides a surface which will abut against a target tissue or prosthetic which may help to prevent overdriving of the surgical fastener through the intended underlying materials.

In one embodiment, the surgical fasteners include a distally extending coil body including one or more coil windings attached to a head with a through hole including an internal thread or threads. The coil body may have a cylindrical shape with a circular cross section, though other shapes are possible including a triangular, rectangular, or any other appropriately shaped cross section. One or more of the surgical fasteners may be loaded in a corresponding deployment device. The deployment device may include a stationary or movable mandrel for holding the one or more fasteners. The mandrel may also include an externally threaded portion located at a distal end of the mandrel. In such an embodiment, the externally threaded portion of the mandrel is constructed and arranged to engage the internal threading of the through hole of the one or more fasteners. To deploy the one or more fasteners, a rotator may selectively rotate the one or more fasteners relative to the mandrel. As the one or more fasteners are rotated relative to the mandrel, the threaded portion of mandrel applies a distally directed force to the internal threading of the fastener heads to move the one or more fasteners in a distal direction and sequentially deploy the one or more surgical fasteners into an underlying prosthetic and/or tissue.

Figure 8A:
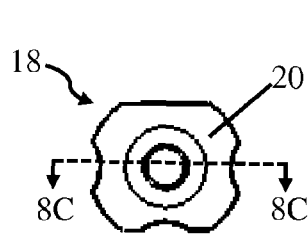
FIG. 8A is a schematic top view of a coil fastener including a head.
Figure 8B:
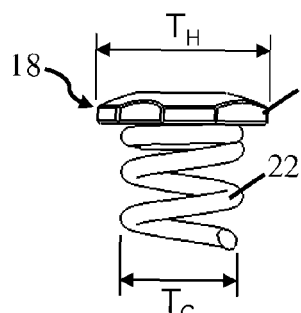
FIG. 8B is a schematic front view of the coil fastener including a head of FIG. 8A.
Figure 8C:
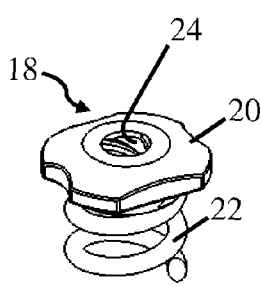
FIG. 8C is a schematic cross-sectional view of the coil fastener including a head of FIG. 8A.
Figure 8D:
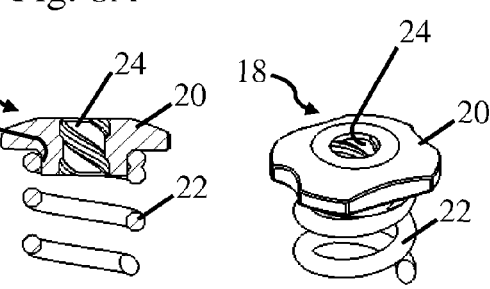
FIG. 8D is a schematic perspective view of the coil fastener including a head of FIG. 8A.

For the purposes of this application, a transverse dimension of the coil body or head generally refers to a dimension of the coil body or head within a plane that is perpendicular to a long axis of the surgical fastener when it is assembled (e.g. a diameter of a cylindrical coil body, a width of a rectangular head, the length of a side of a triangular coil body, etc . . . ). For example, an outer transverse dimension of the coil body would refer to the lateral distance between opposing outer surfaces of the coil body and an inner transverse dimension of the coil body would refer to the lateral distance between opposing interior surfaces of the coil body. The outer transverse dimensions of the head $T_H$ and coil body $T_C$ in two possible embodiments are illustrated in FIGS. 4B and 8B and correspond to the width of the head and the diameter of the coil body. It should be noted that in embodiments in which the head and/or the coil body are noncircular, the head and/or coil body may have both minimum and maximum transverse dimensions.

In view of the above, depending on the particular application, a transverse dimension of the distally extending coil body may be varied to offer different clinical benefits associated with the surgical fastener. For example, in one embodiment, the distally extending coil body has an inner transverse dimension that is approximately the same as a pitch diameter of the threading within the through hole of the fastener head. In such an embodiment, the distally extending coil body engages the corresponding external threading on the mandrel. Further in some embodiments the coil body may extend through the through hole of the fastener head to form the internal threading of the fastener head. In the above embodiment, the coil body is engaged with, and is thus supported by, the mandrel along its entire length which may help to guide and stabilize the coil body of the surgical fastener during deployment. Without wishing to be bound by theory, supporting the coil body during deployment may aid in preventing unwanted buckling or compression of the surgical fastener during deployment. Additionally, a surgical fastener including a coil body with a smaller ratio of coil transverse dimension to fastener head transverse dimension may provide increased mechanical advantage during deployment when a rotator applies a torque to the head of such a surgical fastener.

In another embodiment, a minimum inner transverse dimension of the distally extending coil body is larger than a maximum transverse dimension of the through hole and a maximum outer transverse dimension of the threaded portion of the mandrel. Providing a surgical fastener with a larger minimum coil body transverse dimension allows the surgical fastener to engage larger tissue areas, but the surgical fastener may exhibit decreased mechanical advantage during deployment as compared to the above embodiment because the coil transverse dimension to head transverse dimension ratio is larger. Further, because the distally extending coil bodies have a minimum inner transverse dimension larger than the maximum outer transverse dimension of the threaded portion of the mandrel, they will not be engaged with the mandrel to support the surgical fasteners thereon. Instead, the surgical fasteners are supported on the threaded portion of the mandrel solely by the internal threading located in the through holes of the individual fastener heads. Since the distally extending coil body of the surgical fastener is not supported on the corresponding mandrel, the individual coil bodies may be subject to compression and/or buckling during deployment. Therefore, in some embodiments, it may be desirable to provide one or more guide features associated with the surgical fasteners to avoid buckling and/or compression of the distally extending coil bodiess and ensure proper insertion into tissue during deployment.

It should be understood that the coil bodies and heads of the surgical fasteners may be made from any appropriate materials or combination of materials including various appropriate metals and polymers. Additionally, the material may be selected such that the surgical fastener is nonabsorbable or bioabsorable as the current disclosure is not so limited. For example, the distally extending coil body and the head may be made from: stainless steels such as 316L stainless steel; nickel titanium based alloys such as nitinol; polypropylene; high density polyurethane; ultrahigh molecular weight polyethylene (UHMWPE); nylon; polyester; magnesium; zinc; polylactic acid; polyglycolic acid; or any other appropriate material.

In addition to the surgical fasteners, the various components of the deployment device, including the mandrel and rotator, may be made from any appropriate material or combination of materials including various appropriate metals and polymers. Appropriate materials include, but are not limited to: stainless steels such as 316L stainless steel; nickel titanium based alloys such as nitinol; polypropylene; high density polyurethane; ultrahigh molecular weight polyethylene (UHMWPE); nylon; polyester; or any other appropriate material.

For the sake of clarity, the currently disclosed embodiments are directed to a laparoscopic device. However, the current disclosure is not limited to laparoscopic devices. Instead, the currently disclosed surgical fasteners and associated deployment devices may be used with any appropriate device capable of deploying a fastener into tissue. For example, any of the currently disclosed components, or combination of disclosed components, could be incorporated into an endoscopic device, a borescopic device, a catheter, a surgical instrument for use in "open" procedures, or any other appropriate surgical instrument. Additionally, the deployment device may be loaded with one or more fasteners prior to being provided to an end user, or it may be constructed to allow the user to load one or more fasteners.

Turning now to the figures, specific embodiments of the surgical fasteners and the associated deployment devices are described in more detail. However, it should be understood, that embodiments different from those depicted in the figures are contemplated.

FIG. 1 depicts a deployment device in the form of a laparoscopic surgical instrument 2 for deploying one or more surgical fasteners. The deployment device 2 includes a handle 4 at a proximal end of the device. The handle includes a trigger 6. The deployment device also includes an outer elongated shaft 16 extending in a distal direction from the handle 4. When the trigger 6 is actuated, a surgical fastener is deployed from a distal tip of the elongated shaft 16. It should be understood, that the deployed surgical fastener may be deployed into any appropriate prosthetic, bone, and/or tissue. For example, in one embodiment, a surgical fastener can be deployed into a soft tissue repair fabric, such as a surgical mesh, as well as an underlying tissue for repairing a hernia.

FIG. 2 depicts an exploded view of the deployment device 2 of FIG. 1. As depicted in the figure, the deployment device includes a mandrel 10, a rotator 14, and an outer elongated shaft 16. The mandrel 10 includes a threaded portion 12 for supporting one or more surgical fasteners, not depicted. When assembled, the mandrel 10 is disposed within the rotator 14 which is disposed in the outer elongated shaft 16. The trigger 6 is coupled to the rotator 14 via a transmission 8 such that actuation of the trigger 6 rotates the rotator 14 relative to the mandrel 10. As described in more detail below, this rotation of the rotator 14 relative to the mandrel 10 rotates the surgical fasteners disposed on the threaded portion 12 of the mandrel, not depicted. Rotation of the surgical fasteners relative to the threaded portion 12 of the mandrel displaces the surgical fasteners in a distal direction and deploys a distal most fastener into a prosthetic and/or tissue. It should be understood, that the rotator 14 and transmission 8 may be embodied in any number of different ways in order to rotate the fasteners relative to the mandrel 10. Therefore, it should be understood, that the current disclosure is not limited to only the rotator 14 and transmission 8 depicted in the figures and described below.

In one embodiment, the elongated shaft 16 is articulable. In such an embodiment, it is desirable that the mandrel 10 and the rotator 14 be designed to accommodate articulation of the elongated shaft 16 while still being capable of deploying a surgical fastener. This may be provided in any number of ways. For example, in one embodiment, rotatable links and/or slots may be provided along a portion of the mandrel and/or rotator length in the articulable portion of the device. Alternatively, the mandrel and/or rotator may be made from a flexible material, or include a flexible material within the articulated portion to permit rotation of the rotator when articulated. In yet another embodiment, the rotator and mandrel may be made from rigid materials located in a rigid distal portion of the elongated shaft that articulates about a joint. A transmission may then be used to transmit power from the trigger and through the articulating joint to deploy a surgical fastener. Other embodiments to permit articulation of the deployment device are also possible. Further embodiments in which the deployment device is not articulable are also possible.

In some embodiments, the mandrel 10 is held rotationally and axially stationary relative to the handle 4 and/or the outer elongated shaft 16. However, the mandrel 10 might also be held rotationally stationary relative to the handle 4 and/or outer elongated shaft 16 and may be movable in a proximal and distal direction. In such an embodiment, the mandrel 10 may advance in a distal direction during deployment of a surgical fastener to extend the mandrel outside of the distal end of the outer elongated shaft 16. The mandrel 10 may then retract in a proximal direction after a surgical fastener has been deployed. The mandrel may include either a pointed distal tip 26 to aid in positioning the fastener relative to soft and/or hard tissues, or the distal tip 26 may be blunt as the current disclosure is not limited in this fashion.

In some embodiments, it may be desirable to increase the deployment and/or retention force of the surgical fasteners relative to the mandrel 10. Consequently, the threaded portion 12 of the mandrel and corresponding threading on the surgical fasteners may include multiple threads. For example, the threaded portion 12 of the mandrel and the internal threading of the surgical fasteners, not depicted, may include at least two threads, three threads, four threads, or any other desirable number of threads as the current disclosure is not limited in this respect. Without wishing to be bound by theory, in addition to providing increased retention and deployment forces, the multiple threads may also help to stabilize the surgical fasteners on the mandrel as they are distally displaced through the elongated shaft and subsequently deployed into an underlying prosthetic and/or tissue.

Having generally described the various components of the deployment device, FIG. 3 depicts a close-up exploded perspective view of the distal end of one embodiment of the mandrel 10 and the rotator 14. A plurality of surgical fasteners 18 are disposed on the threaded portion 12 of the mandrel. As depicted in the figures, the surgical fasteners 18 include a head 20 and a distally extending coil body 22 attached to the head. In this embodiment, the head 20 and distally extending coil body 22 of each surgical fastener 18 are constructed and arranged to engage with the threaded portion 12 of the mandrel. However, as described in more detail below, embodiments in which the distally extending coil body 22 has a minimum inner transverse dimension larger than the threaded portion 12 of the mandrel, and thus is not engaged with the mandrel, also are contemplated. As indicated by the arrow, the mandrel 10, as well as the plurality of surgical fasteners 18 disposed thereon, are positioned within the rotator 14. As described in more detail below, the depicted rotator 14 is an outer drive cannula with a cross-sectional profile that complements a shape and size of the fastener heads 20. Therefore, rotation of the rotator 14 relative to the mandrel rotates the fasteners 18 relative to the threaded portion 12 of the stationary mandrel. This rotation of the surgical fasteners 18 relative to the threaded portion 12 of the mandrel, distally displaces the one or more surgical fasteners and deploys a distal most surgical fastener into an underlying prosthetic and/or tissue.

Figure 4A:
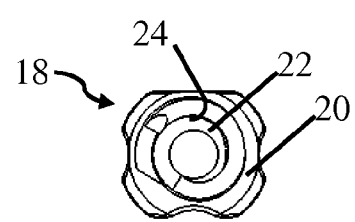
FIG. 4A is a schematic top view of a coil fastener including a head.
Figure 4B:
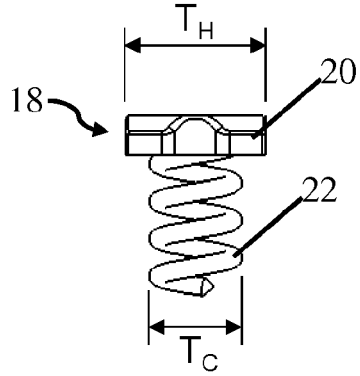
FIG. 4B is a schematic front view of the coil fastener including a head of FIG. 4A.
Figure 4C:
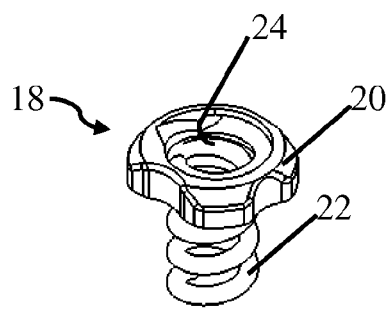
FIG. 4C is a schematic perspective view of the coil fastener including a head of FIG. 4B.

FIGS. 4A-4C depict one embodiment of a surgical fastener 18 for use with the deployment device described above. In the depicted embodiment, the surgical fastener 18 includes a distally extending coil body 22 that is attached to a head 20 including a through hole 24 with an internal thread. Further, the inner transverse dimension of the distally extending coil body 22 is selected such that one or more of the individual coil windings of the distally extending coil body 22 engages with the threaded portion of the mandrel along either a portion or substantially the entire length of the coil body 22 distally extending from the head 20. In some embodiments, the coil body 22 may pass through the through hole 24 to form the internal threading located therein. The coil body 22 is attached to the head 20 using any appropriate method. For example, the coil body 22 may be integrally formed with the head 20 or it may be manufactured separately and attached using a compression fit, adhesives, mechanical interlocking features, threading, interference fits, or any other appropriate method.

Figure 5:
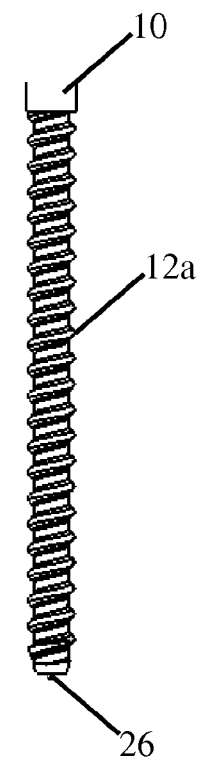
FIG. 5 is a schematic front view of the threaded portion of a stationary inner mandrel.

FIG. 5 depicts an embodiment of a mandrel 10 including a threaded portion 12a for use with the surgical fastener depicted in FIGS. 4A-4C. The threaded portion 12a includes a single thread with the same pitch as the coil windings of the coil body 22. Additionally, the threaded portion 12a is sized to engage both the internal threading of the through hole 24 and the distally extending coil windings of the coil body 22 as well. While a blunted distal tip 26 is depicted, a pointed tip might also be used.

Figure 6A:
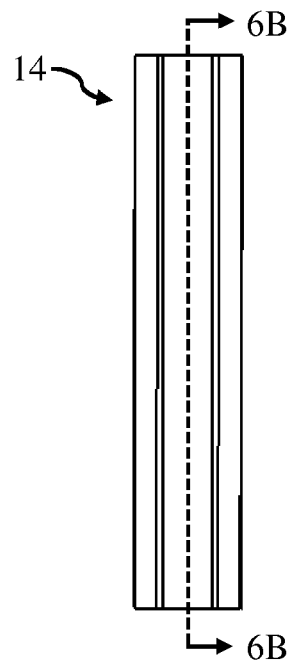
FIG. 6A is a schematic front view of an outer drive cannula.
Figure 6B:
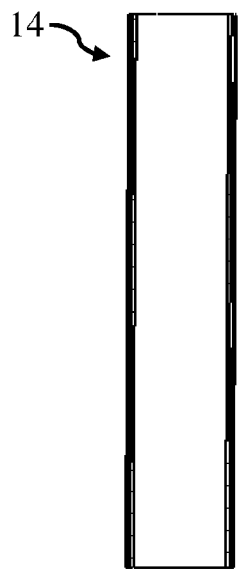
FIG. 6B is a schematic cross-sectional view of the outer drive cannula of FIG. 6A taken along line 6B-6B.
Figure 6C:
FIG. 6C is a schematic perspective view of the outer drive cannula of FIG. 6A.

As best shown in FIG. 4A, the head 20 of the surgical fastener has a shape including a series of flats and rounded portions. In order to engage the heads 20 of the surgical fasteners, the rotator 14, corresponding to the distally extended elongated outer drive cannula depicted in FIGS. 6A-6C, includes an internal cross-sectional shape that complements the shape and size of the heads 20 of the surgical fasteners. The specific shape of the heads 20 and the internal cross-section of the rotator 14 is selected such that rotation of the rotator 14 rotates the fasteners 18 relative to the mandrel 10 with minimal or no slip. While a specific shape is depicted in the figures, other shapes are also possible. For example, the fastener heads and corresponding cross-sectional shape of the rotator may also correspond to a triangle, a quadrilateral, a pentagon, an asymmetrical shape, or any other appropriate shape capable of transferring rotation of the rotator 14 to the fasteners 18. It should be understood that embodiments in which the rotator only complements a portion of the shape and size of the heads also are contemplated.

Figure 7C:
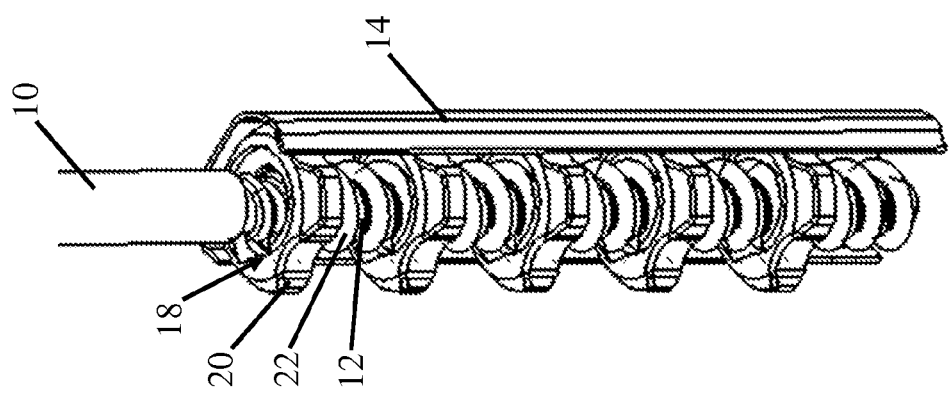
FIG. 7C is a perspective view of the cross section of the outer drive cannula as well as the stationary inner mandrel and the plurality of fasteners depicted in FIG. 7A.
Figure 7B:
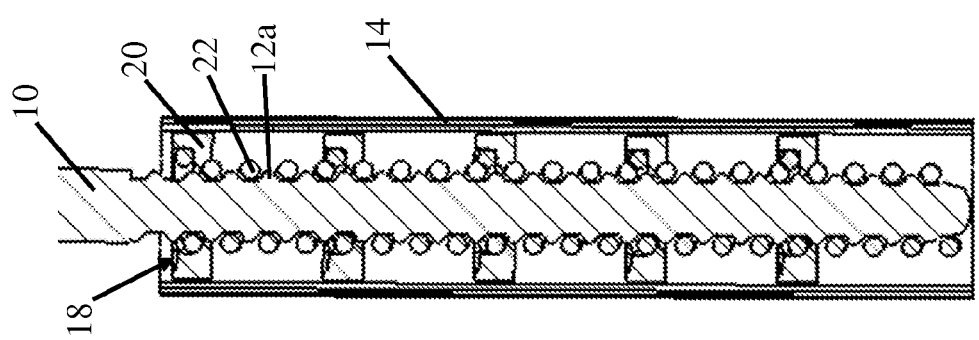
FIG. 7B is a schematic cross-sectional view of the outer drive cannula, the stationary inner mandrel, and the plurality of fasteners of FIG. 7A.
Figure 7A:
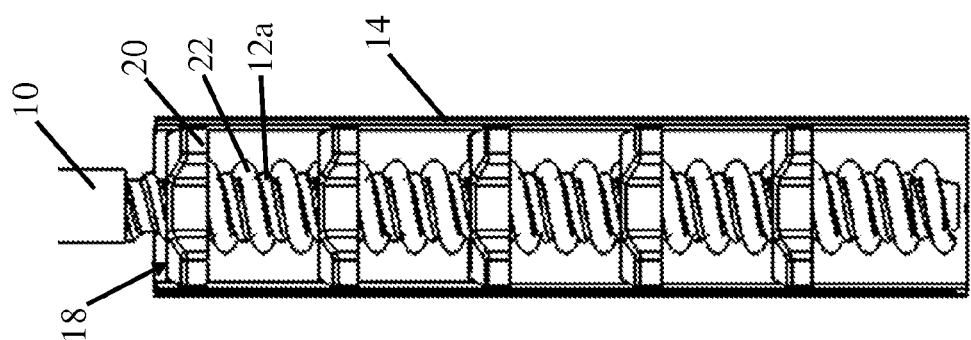
FIG. 7A is a schematic cross-sectional view of an outer drive cannula with a stationary inner mandrel and a plurality of fasteners positioned therein.

FIGS. 7A-7C depict various cross-sectional views of the assembled mandrel 10, rotator 14, and a plurality of surgical fasteners 18 to help illustrate how the deployment device functions. As illustrated in the figures, the mandrel is disposed inside of the rotator 14 with the plurality of surgical fasteners 18 disposed thereon. In the depicted embodiment, the heads 20 of the surgical fasteners are engaged with the internal cross-section of the rotator 14 and the coil windings of the coil body 22 are engaged with the thread portion 12a of the mandrel along their entire lengths. During actuation, the rotator 14 is rotated relative to the mandrel 10. As the rotator 14 is rotated, the internal cross-section of the rotator applies a torque to the head 20 of each fastener 18. This torque rotates the fasteners 18 relative to the mandrel 10. Due to the internal threading of the coil bodies and/or heads engaging the threaded portion 12a of the mandrel, rotating the heads will apply a distally directed force to the internal threading of the surgical fasteners 18 and displace the surgical fasteners 18 in a distal direction. As the surgical fasteners 18 are displaced in a distal direction, a distal most fastener is displaced out of the distal end of the deployment device and into an underlying prosthetic and/or tissue.

In some instances, it may be beneficial to provide either a compressive or tensile force to a prosthetic and/or tissue that the surgical fastener is deployed into. Therefore, in some embodiments, the pitch of the coil windings of the coil body may be different from a pitch of the internal threading of the through hole and the associated threaded portion of the mandrel it is engaged with. For example, the coil windings might have a pitch in a relaxed position that is less than a pitch of the internal threading of the through hole and the associated threaded portion of the mandrel. In such an embodiment, the coil body may be deformed to an elongated state while it is positioned on the threaded portion of the mandrel. After the coil body is deployed into tissue, the coil body may contract towards its relaxed position and provide a compressive force to the prosthetic and/or tissue it is deployed into. Similar to the above, in order to provide a tensile force to the prosthetic and/or tissue, the coil windings may have a pitch that is greater than a pitch of the threaded corresponding portion of the mandrel.

FIGS. 8A-8D and 9 depict another embodiment of a surgical fastener and an associated deployment device. Similar to the above, the surgical fastener 18 includes a distally extending coil body 22 attached to a head 20 including a threaded through hole 24. However, in this embodiment, an inner transverse dimension of the coil body 22 is greater than a transverse dimension of the through hole 24 and an associated threaded portion 12b of the mandrel depicted in FIG. 9. While the coil body 22 may be attached to the head 20 in any appropriate fashion, in the depicted embodiment, a proximal end of the coil body 22 creates an compression fit with a shoulder 28 of the head.

In this embodiment, since the coil body 22 is larger than the through hole 24 and the associated threaded portion 12b of the mandrel, the coil does not engage the threaded portion 12b of the associated mandrel. Therefore, the surgical fastener 18 will be solely supported on the threaded portion of the mandrel by the internal threading located in the through hole 24. In such an embodiment, the internal threading of the through hole 24 may include multiple threads to increase the stability of the surgical fastener on the mandrel as well as the force applied during deployment. In the depicted embodiment, the surgical fastener 18 includes two internal threads within through hole 24.

To further increase stability and the force applied to the surgical fasteners 18 during deployment, it may also be desirable to provide at least a minimum amount of engagement between the internal threading of the through hole 24 and the associated threaded portion 12b of the mandrel. For example, a fastener head including a single thread might include at least a full turn of the thread. Similarly, a fastener head including two threads might include at least a half turn of each thread to provide at least a combined full turn of engagement with the multiple threads. It should be understood that other numbers of threads and either greater or lesser amounts of combined thread engagement are also possible.

Figure 9:
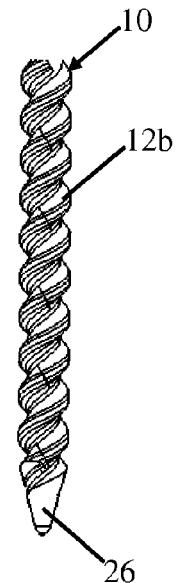
FIG. 9 is a schematic front view of the threaded portion of a stationary inner mandrel.

FIG. 9 presents an embodiment of a mandrel 10 including a threaded portion 12b configured to engage with the internal threading of the through hole 24 of the surgical fastener depicted in FIGS. 8A-8D. Since the surgical fastener depicted in the figures has two internal threads, the threaded portion 12b of the mandrel also has two corresponding external threads as well. Additionally, the mandrel 10 also includes a pointed distal tip 26. As noted above, the pointed distal tip can be inserted into a prosthetic and/or tissue to aid in positioning the fastener. In such an embodiment, the mandrel 10 may either be displaced to extend out of a distal end of an associated deployment device, or it may fixed such that it extends out of the distal end of an associated deployment device. While a pointed distal tip has been depicted with the current embodiment, a blunt tip might also be used.

Figure 10A:
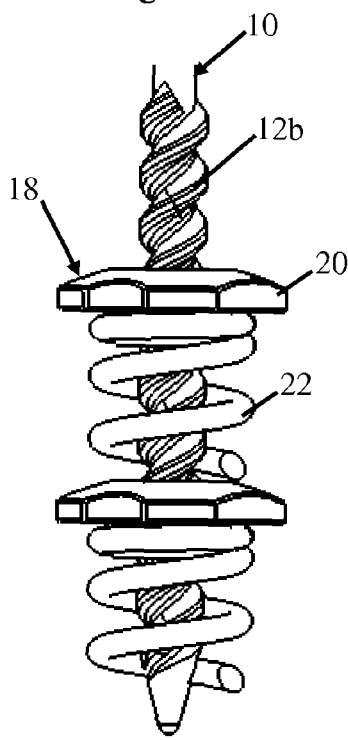
FIG. 10A is a front view of a stationary inner mandrel and a plurality of fasteners positioned thereon.
Figure 10B:
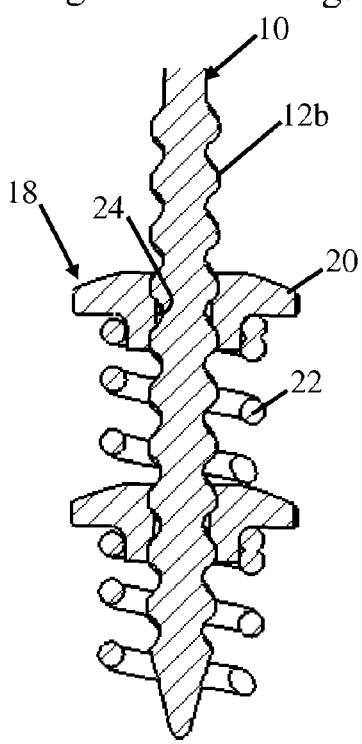
FIG. 10B is a schematic cross-sectional view of the stationary inner mandrel and the plurality of fasteners of FIG. 10A.
Figure 10C:
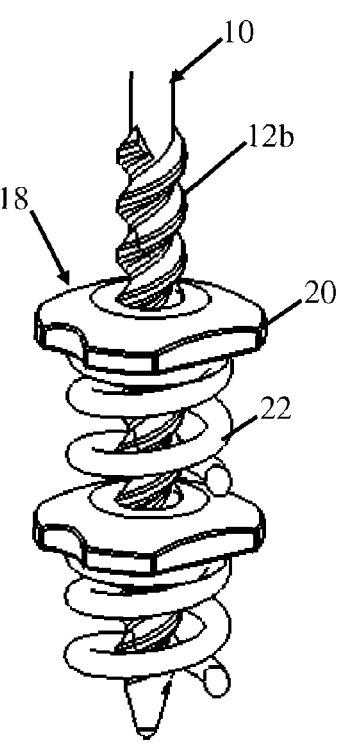
FIG. 10C is a schematic perspective view of the stationary inner mandrel and the plurality of fasteners of FIG. 10A.

FIGS. 10A-10C depict the surgical fasteners 18 of FIGS. 8A-8D including a coil body that has a larger minimum inner transverse dimension than a maximum outer transverse dimension of the associated through hole and/or threaded portion of the mandrel. To aid in visualization, an associated rotator is not depicted. Similar to the other embodiment described above, the internal threading of the through hole 24 of each surgical fastener 18 is engaged with the threaded portion 12b of the mandrel. However, as noted above, the distally extending coils 22 are not engaged with the threaded portion 12b of the mandrel because it has a larger inner transverse dimension. So, as the surgical fasteners 18 are rotated relative to the mandrel 10, the threaded portion 12b of the mandrel will apply a distally directed force to the internal threading located in the through hole 24 of each surgical fastener, but will not interact with the distally extending coil bodies directly. Therefore, similar to the other embodiment, this results in the surgical fasteners undergoing both rotation and displacement in a distal direction to deploy the surgical fasteners from the distal end of a deployment device and into a desired prosthetic and/or tissue.

While a particular rotator with a particular cross-sectional shape has been depicted in the figures and described above, it should be understood that any appropriate rotator capable of rotating the surgical fasteners relative to the mandrel may be used. Appropriate rotators may also include: different cross-sectional shapes; distally extending arms that engage corresponding features on the surgical fasteners; a rotator that only engages a portion of the cross-section of the surgical fasteners; keyed features, combinations of the above, and any other appropriate rotator.

In addition to the above, while the depicted surgical fasteners have a fastener head with a particular cross-sectional shape, it should be understood that any appropriate fastener head capable of being engaged by the rotator may be used. For example, other types of features and/or shapes, such as slots, holes, grooves, tabs, and/or combinations of the above, might be used to associate the surgical fasteners with the rotator.

In other embodiments, it may be desirable to increase the retention force of the surgical fasteners in tissue. One possible way in which to do this is to use a coil body including multiple parallel and distally extending coil windings attached to the fastener head. Therefore, in some embodiments, the surgical fasteners may include at least two, three, or any desirable number of parallel and distally extending coil windings attached to the fastener head.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A deployment device comprising:
   a handle;
   a shaft extending distally from the handle;
   one or more surgical fasteners disposed in the shaft, the one or more surgical fasteners including a head and a separately formed coil body attached to the head, the coil body distally extending from the head with at least one coil winding attached to the head, wherein the head includes a through hole with an internal thread, wherein the at least one coil winding encircles a hollow opening, and wherein the coil body forms at least a portion of the internal thread of the head;
   a mandrel including a threaded portion, wherein the threaded portion is engaged with the internal thread of the head of the one or more surgical fasteners, and wherein the coil body of the one or more fasteners is engaged with the threaded portion of the mandrel; and
   a rotator associated with the one or more surgical fasteners, wherein the rotator selectively rotates the one or more surgical fasteners relative to the mandrel to displace the one or more surgical fasteners in a distal direction.

2. The deployment device of claim 1, wherein both the threaded portion of the mandrel and the internal thread include at least two threads.

3. The deployment device of claim 1, wherein the mandrel is stationary.

4. The deployment device of claim 3, wherein the mandrel is rotationally stationary.

5. The deployment device of claim 4, wherein the mandrel reciprocates in a proximal and distal direction.

6. The deployment device of claim 1, wherein the mandrel includes a sharp distal tip.

7. The deployment device of claim 1, wherein a pitch of the at least one coil winding of the coil body is different from a pitch of the internally threaded through hole and/or the threaded portion of the mandrel.

8. The deployment device of claim 1, wherein the threaded portion is located at a distal end of the mandrel.

9. The deployment device of claim 1, wherein at least a portion of the coil body located distally from the head is threaded to and engaged with the threaded portion of the mandrel.

10. The deployment device of claim 1, wherein the mandrel includes a blunt distal tip.

11. The deployment device of claim 1, wherein the coil body of the one or more surgical fasteners includes at least two separate coil windings that are parallel to each other and extend distally from the head.

12. The deployment device of claim 1, wherein the coil body of the one or more surgical fasteners is elongated relative to its relaxed length when the one or more surgical fasteners are engaged with the mandrel.

13. The deployment device of claim 1, wherein a minimum inner transverse dimension of the coil body is equal to a pitch diameter of the internal thread.

14. The deployment device of claim 13, wherein a pitch of the at least one coil winding of the coil body is greater than a pitch of the internally threaded through hole and/or the threaded portion of the mandrel.

15. The deployment device of claim 13, wherein a pitch of the at least one coil winding of the coil body is less than a pitch of the internally threaded through hole and/or the threaded portion of the mandrel.

* * * * *